United States Patent [19]
Cheung et al.

[11] Patent Number: 6,100,231
[45] Date of Patent: Aug. 8, 2000

[54] BIPHENYL BASED SOLVENTS IN BLOOMING TYPE HARD SURFACE CLEANERS

[75] Inventors: Tak Wai Cheung, Princeton Junction; Dennis Smialowicz, Waldwick, both of N.J.

[73] Assignee: Reckitt & Colman Inc., Wayne, N.J.

[21] Appl. No.: 09/044,552

[22] Filed: Mar. 19, 1998

[30] Foreign Application Priority Data

Nov. 28, 1997 [GB] United Kingdom .................. 9725098

[51] Int. Cl.[7] ........................................ C11D 1/75
[52] U.S. Cl. .................. 510/433; 510/438; 510/461; 510/503
[58] Field of Search ................... 510/191, 238, 510/239, 433, 438, 461, 503

[56] References Cited

U.S. PATENT DOCUMENTS

| | | | |
|---|---|---|---|
| 3,617,213 | 11/1971 | Britt et al. | 8/175 |
| 3,728,078 | 4/1973 | Freshwater et al. | 8/174 |
| 3,787,181 | 1/1974 | Dellian et al. | 8/174 |
| 4,016,098 | 4/1977 | Saeki et al. | 252/316 |
| 4,167,504 | 9/1979 | Davis et al. | 260/33.6 |
| 5,051,327 | 9/1991 | Osawa et al. | 430/49 |
| 5,266,082 | 11/1993 | Sanders | 44/357 |
| 5,371,105 | 12/1994 | Damo et al. | 514/469 |
| 5,384,059 | 1/1995 | Klein et al. | 252/73 |
| 5,538,662 | 7/1996 | Klier et al. | 252/122 |
| 5,591,708 | 1/1997 | Richter | 510/463 |
| 5,674,517 | 10/1997 | Carpenter | 424/405 |

FOREIGN PATENT DOCUMENTS

| | | | |
|---|---|---|---|
| 0 040 882 A1 | 12/1981 | European Pat. Off. | |
| 195 37 782 A1 | 4/1997 | Germany | A01N 65/00 |
| 2 304 111 | 3/1997 | United Kingdom . | |
| 2 304 112 | 3/1997 | United Kingdom . | |
| 2 304 115 | 3/1997 | United Kingdom . | |
| 2 304 728 | 3/1997 | United Kingdom . | |
| WO96/06153 | 2/1996 | WIPO | C11D 3/00 |
| WO97/06230 | 2/1997 | WIPO | C11D 1/65 |

OTHER PUBLICATIONS

Copy of GB Search Report for GB Patent Application No. 9725098.9 dated Feb. 27, 1998.
Technical Leaflet titled "NUSOLV ABP Solvents" from Ridge Technologies, Ridgewood, Nj. dated Nov. 1992.

*Primary Examiner*—J R Hardee
*Attorney, Agent, or Firm*—Fish & Richardson P.C.

[57] ABSTRACT

Aqueous concentrated liquid hard surface cleaning compositions which include: a pine oil constituent; organic solvent constituent; binary co-solvent system comprising alkyl biphenyl solvent and a co-solvent; and amine oxide surfactant constituent, and optionally but desirably at least one optional constituent.

The liquid hard surface cleaning compositions feature excellent initial blooming characteristics, as well as good long term blooming retention.

12 Claims, No Drawings

BIPHENYL BASED SOLVENTS IN BLOOMING TYPE HARD SURFACE CLEANERS

The present invention relates to blooming type hard surface cleaning compositions. More particularly the present invention relates to concentrated liquid compositions which are normally diluted in a larger volume of water to form a working solution therefrom, and which exhibit a blooming effect when diluted.

Blooming is a property exhibited by dilutable compositions such as known cleaning compositions, specifically pine-oil type cleaning compositions which contain a significant amount (generally at least about 5% and more) of pine oil. Certain phenolic disinfectant compounds, such as LYSOL® disinfectant concentrate (Reckitt & Colman, Inc., Montvale N.J.) also exhibit such a blooming property. Other known-art compositions which do not provide a disinfecting benefit but which are blooming type cleaning compositions are also known, such as PINE-SOL® (Clorox Co., Oakland Calif.). Blooming may be characterized as the formation of milky, creamy or cloudy appearance which is manifested when a dilutable composition is added to a larger volume or quantity of water. Blooming is an important characteristic from a consumer standpoint as it provides a visual indicator and impression to the consumer that the concentrated product contains active cleaning constituents which are released upon addition of the concentrate to a volume of water. Such is an important visual indicator of apparent efficacy of a concentrated product.

It has now been found that it is now possible to produce certain concentrate compositions utilizing these selected constituents in particular formulations which provide blooming type cleaning compositions in a concentrated liquid form which provide a good blooming effect. The "blooming" observed may be described as the change of the water's appearance from essentially colorless and transparent to that of a milky white or milky yellowish white, cloudy appearance. This effect is also sometimes referred to as the "break". Such blooming is a highly desirable in blooming type cleaning compositions as consumer/end user expectations associate cleaning effectiveness with the extent and degree of this blooming upon formation of a cleaning composition. Such blooming is particularly desirable in compositions where the blooming characteristic in an aqueous dilution is long lasting.

Accordingly it is an object of the invention to provide an aqueous concentrated liquid hard surface cleaning composition which blooms when added to a larger volume of water which comprises the following constituents:

pine oil constituent;

organic solvent constituent;

binary co-solvent system comprising an alky biphenyl solvent and a co-solvent;

an amine oxide surfactant constituent;

optionally but desirably at least one optional constituent selected from: chelating agents, coloring agent, light stabilizers, fragrances, thickening agents, hydrotropes, pH adjusting agents, pH buffers one or more detersive surfactant constituents which do not undesirably affect the blooming characteristics of the concentrate composition, as well as others known the art and useful in similar compositions. The one or more optional constituents are selected to be present, and are included in amounts which do not undesirably affect the overall blooming characteristics of the present inventive compositions.

In preferred embodiments the concentrate compositions provide excellent initial blooming characteristics in 'as mixed' dilutions with water, but also exhibit good retention of blooming characteristics over a longer time period, viz., days and weeks.

It is a further object of the invention to provide such a concentrated liquid hard surface cleaning composition wherein the composition exhibits a blooming effect when diluted in a larger volume of water.

It is a still further object of the invention to provide working solutions formed from concentrated liquid hard surface cleaning compositions which exhibit a blooming effect when diluted in a larger volume of water, particularly where the dilutions retain their blooming characteristic over an extended period, i.e., several days, and even several weeks.

It is among the further object of the invention to provide such a concentrated liquid hard surface cleaning composition wherein the composition exhibits good long term stability, i.e., shelf stability in its concentrated form.

The concentrate compositions of the invention comprise a pine oil constituent. Pine oil is an organic solvent, and is a complex blend of oils, alcohols, acids, esters, aldehydes and other organic compounds. These include terpenes which include a large number of related alcohols or ketones. Some important constituents include terpineol, which is one of three isomeric alcohols having the basic molecular formula $C_{10}H_{17}OH$. Useful pine oils include synthetic pine oil, and also include steam distilled and sulfate pine oils, and will generally contain a higher content of turpentine alcohols. Other important compounds include alpha- and beta-pinene (turpentine), abietic acid (rosin), and other isoprene derivatives.

Particularly effective pine oils which are presently commercially available include Glidco® Pine Oil™ 60 (believed to contain approximately 60% terpene alcohols), Glidco® Pine Oil 80 (believed to contain approximately 80% terpene alcohols) Glidco® Pine Oil 150 (believed to contain approximately 85% terpene alcohols); Glidco® Terpene SW (believed to contain approximately 75% terpene alcohols); as well as Glidco® Terpineol 350 (believed to contain approximately 100% terpene alcohols). Each of these may be obtained from available from Glidco Organics Corp., Jacksonville, Fla. (USA). Other products which can contain up to 100% pure alpha-terpineol, may also be used in the present invention.

The pine oil constituent may be present in the concentrate compositions in amounts of from about 0.001% by weight to up to about 20% by weight, preferably about 0.1–15% by weight, most preferably in amount of between 1–10% pine oil by weight. Preferred of these are pine oil preparations which comprise at least about 50% terpene alcohols, more desirably at least about 60% terpene alcohols, and more preferably those which comprise at least about 80% terpene alcohols. As with all of the weight percentages of the constituents described, the weight percentages are indicative of the weight percentages of the actives in a constituent containing preparation.

A further constituent according to the invention is an organic solvent which is present in addition to the pine oil which is itself known to be an organic solvent and assists in improves the dispersability and/or miscibility of the water insoluble pine oil in water. The organic solvent may also improve the miscibility of further constituents according to the present invention, including any water insoluble or poorly soluble constituents. Many useful organic solvent which are known to be useful in dispersing pine oil in water may be used; virtually any may be used as long as it does not undesirably disrupt the favorable characteristics of the invention, especially the blooming characteristic. Mixtures of two or more organic solvents may also be used as the organic solvent constituent.

Useful organic solvents are those which are at least partially water-miscible such as alcohols, water-miscible ethers (e.g. diethylene glycol diethylether, diethylene glycol dimethylether, propylene glycol dimethylether), water-miscible glycol ether (e.g. propylene glycol monomethylether, propylene glycol mono ethylether, propylene glycol monopropylether, propylene glycol monobutylether, ethylene glycol monobutylether, dipropylene glycol monomethylether, diethyleneglycol monobutylether), lower esters of monoalkylethers of ethyleneglycol or propylene glycol (e.g. propylene glycol monomethyl ether acetate) all commercially available from Union Carbide, Dow Chemicals or Hoescht. Mixtures of organic solvents can also be used.

Particularly useful organic solvents include glycols such as alkylene glycols such as propylene glycol, and glycol ethers. Examples of such glycol ethers include those having the general structure R'—O—R"—OH, wherein R' is an alkoxy of 1 to 20 carbon atoms, or aryloxy of at least 6 carbon atoms, and R" is an ether condensate of propylene glycol and/or ethylene glycol having from one to ten glycol monomer units. Examples of such useful glycol ethers include propylene glycol methyl ether, dipropylene glycol methyl ether, tripropylene glycol methyl ether, propylene glycol isobutyl ether, ethylene glycol methyl ether, ethylene glycol ethyl ether, ethylene glycol butyl ether, diethylene glycol phenyl ether, propylene glycol phenol ether, and mixtures thereof. Preferred are ethylene glycol n-butyl ether, diethylene glycol n-butyl ether, propylene glycol and mixtures thereof. Most preferably, the organic solvent constituent includes propylene glycol as the sole glycol or glycol ether present in the composition. Such glycol ethers recited above are presently commercially available from a number of sources including in the DOWANOL™ glycol ether from The Dow Chemical Company, Midland Mich. (USA).

Further particularly useful organic solvents monohydric (straight chained or branched) primary, secondary or tertiary lower aliphatic alcohols, especially $C_1-C_6$ aliphatic primary and secondary alcohols, of which isopropanol is particularly preferred.

It has generally been found the addition of only a minimum effective amount which is found to be effective in dispersing or solubilizing the pine oil constituent and any other aqueous insoluble or poorly soluble constituents in the concentrate compositions is desirably used. Such is due to desire to reduce the amount of volatile organic constituents in the concentrate compositions of the invention, which volatile organic constituents are desirably minimized from an environmental standpoint. The present inventors have found that inclusion of the organic solvent constituent in amounts of about 0.001% by weight to about 50% by weight have been found to be effective to solubilize the pine oil, as well as in solubilizing other less water soluble constituents present in the concentrate compositions of the invention. Preferably, the organic solvent constituent is present in amounts of from 0.1–40% by weight, and most preferably from about 0.1–35% by weight.

Additionally the inventor has found the according to certain preferred embodiments the organic solvent constituent, comprises, and in certain especially preferred embodiments consist essentially of, both an alkylene glycol such as propylene glycol, and a monohydric lower aliphatic alcohol such as a $C_1-C_6$ aliphatic primary and secondary alcohol, especially isopropyl alcohol.

The inventive compositions further also include a binary co-solvent system comprising alkyl biphenyl solvent and a co-solvent which aids in the solubilization of the biphenyl solvent in an aqueous medium.

The alkyl biphenyl solvent is one which may be generally represented by the formula:

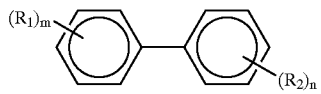

$R_1$ is hydrogen or is a lower alkyl radical, preferably a $C_1-C_{10}$, but more preferably is a $C_1-C_6$ straight chained or branched alkyl radical, $R_2$ is a lower alkyl radical, preferably a $C_1-C_{10}$, but more preferably is a $C_1-C_6$ straight chained or branched alkyl radical, m is an integer from 1–3 inclusive; and, n is an integer from 1–3 inclusive.

Preferably $R_1$ is hydrogen, m is 1, and $R_2$ has any of the values indicated above. More preferably, $R_1$ is hydrogen and m is 1, and $R_2$ is a $C_1-C_6$ straight chained or branched alkyl radical. It is to be understood that mixtures of the compounds indicated above may be used as the biphenyl solvent constituent.

Such alkyl biphenyls are, per se, known to the art, and are described in U.S. Pat. No. 3,787,181. Particularly useful as the alkyl biphenyl solvent are materials presently marketed as NUSOLV ABP solvents (Ridge Technologies Inc., Ridgewood N.J.) described to be a high purity alkyl biphenyls and mixtures thereof, and are also available from Koch Chemical Co.(Corpus Christi, Tex.).

The alkyl biphenyl solvent may be present in the concentrate compositions in amounts of from about 0.001% by weight to up to about 20% by weight, preferably about 0.01–10% by weight, most preferably in amount of between 0.1–8% by weight.

The inventors have observed that the concentrated compositions of the invention are greatly improved with the addition of a co-solvent. This co-solvent aids in the solubilization of the alkyl biphenyl solvent in water is desirably an at least partially water-miscible monohydric primary alcohol, especially a water-miscible monohydric primary $C_8-C_{18}$ alcohol. Particulary effective are cetyl, lauryl and myristyl alcohols. The inventors have found that the inclusion of such alcohols greatly aids in the dissolution of the alkyl biphenyl solvents in the concentrate compositions according to the invention being described herein, which aids in ensuring that clarity of the concentrate composition is maintained which is particularly desirable from a consumer standpoint.

When the co-solvent is one of the at least partially water-miscible monohydric primary alcohols, these may be present in the concentrate compositions in amounts of from about 0.001% by weight to up to about 5% by weight, preferably about 0.01–3% by weight, most preferably in amount of between 0.1–2% by weight.

The concentrate compositions also include one or more amine oxide surfactant constituents. Such amine oxides desirably improve the miscibility of the pine oil constituents in the aqueous phase of the concentrate compositions. Non-limiting examples of useful amine oxide semi-polar non-ionic surfactants include those according to either of the formula:

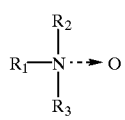

-continued

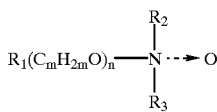

wherein $R_1$ is hydrogen or is an alkyl, 2-hydroxyalkyl, 3-hydroxyalkyl, or 3-alkoxy-2-hydroxypropyl radical where the alkyl and alkoxy parts contain from about 8 to about 18 carbon atoms, $R_2$ and $R_3$ are independently selected from methyl, ethyl, propyl, isopropyl, 2-hydroxyethyl, 2-hydroxypropyl, or 3-hydroxypropyl, m is an integer from 2 to 4, and n is an integer from 0 to about 10. Preferably, the amine oxide semi-polar nonionic surfactants are those according to the formula immediately preceding wherein $R_1$ is an alkyl radical of from 12 to 16 carbon atoms, $R_2$ and $R_3$ are independently selected from methyl or ethyl, m is 2, and n is 0. Specific examples of such useful amine oxide semi-polar nonionic surfactants include cetyl-, myristyl- or lauryl- dimethyl amine oxide or mixtures thereof.

A further useful general class of useful amine oxides which may be included in the amine oxide constituent according to the invention are further alkyl di (lower alkyl) amine oxides in which the alkyl group has about 10–20, and preferably 12–16 carbon atoms, and can be straight or branched chain, saturated or unsaturated. The lower alkyl groups include between 1 and 7 carbon atoms. Examples include those described above, as well as those in which the alkyl group is a mixture of different amine oxides, dimethyl cocoamine oxides, dimethyl (hydrogenated tallow) amine oxides, and myristyl/palmityl dimethyl amine oxides.

A further class of useful amine oxides include alkyl di (hydroxy lower alkyl) amine oxides in which the alkyl group has about 10–20, and preferably 12–16 carbon atoms, and can be straight or branched chain, saturated or unsaturated. Examples are bis(2-hydroxyethyl) cocoamine oxide, bis(2-hydroxyethyl) tallowamine oxide; and bis(2-hydroxyethyl) stearylamine oxide.

Further useful amine oxides include those which may be characterized as alkylamidopropyl di(lower alkyl) amine oxides in which the alkyl group has about 10–20, and preferably 12–16 carbon atoms, and can be straight or branched chain, saturated or unsaturated. Examples are cocoamidopropyl dimethyl amine oxide and tallowamidopropyl dimethyl amine oxide; and Additional useful amine oxides include those which may be referred to as alkylmorpholine oxides in which the alkyl group has about 10–20, and preferably 12–16 carbon atoms, and can be straight or branched chain, saturated or unsaturated.

Exemplary amine oxide surfactant constituents include AO-728 which is described to be a composition containing 50% wt. of bis-(2-hydroxyethyl $C_{12}$–$C_{15}$ alkyloxypropyl) amine oxide (Tomah Products Inc., Milton Wis.), and AMMONYX CDO Special described to be cocoamidopropyl dimethyl amine (Stepan Co., Northfield Ill.).

The amine oxide constituent is present in the inventive concentrate compositions in amounts of up to 30% wt., preferably in amounts of from 0.1–30% wt. and still more prefereably in amounts of from 1–20% wt., yet more preferably 12–18% wt. and most preferably about 13–15% wt., based on the total weight of the concentrate composition.

It is to be understood that both the at least partially water-miscible monohydric primary alcohol and an amine oxide may each be present in the concentrate compositions, and according to certain preferred embodiments both are present.

Water is added in order to provide 100% by weight of the concentrate composition. Water is added in amounts which are sufficient to form the concentrated compositions which amount is sufficient to ensure the retention of a substantially clear characteristic when produced as a concentrate, but at the same time ensuring good blooming upon the addition of the concentrated composition to a further amount of water, or upon the addition of further water to the concentrate. The water may be tap water, but is preferably distilled and/or deionized water. If the water is tap water, it is preferably appropriately filtered in order to remove any undesirable impurities such as organics or inorganics, especially minerals salts which are present in hard water which may thus interfere with the operation of the other constituents of the invention, as well as any other optional components of the liquid concentrates according to the invention.

Other conventional additives known to the art but not expressly enumerated here may also be included in the compositions according to the invention. By way of non-limiting example without limitation these may include: chelating agents, coloring agents, light stabilizers, fragrances, thickening agents, hydrotropes, pH adjusting agents, pH buffers as well as one or more detersive surfactants which do not deleteriously detract from the blooming characteristics of the inventive compositions. Many of these materials are known to the art, per se, and are described in *McCutcheon's Detergents and Emulsifiers*, North American Edition, 1982; *Kirk-Othmer, Encyclopedia of Chemical Technology*, 3rd Ed., Vol. 22, pp. 346–387, the contents of which are herein incorporated by reference. Mixtures of two or more such surface active agents may be incorporated into the inventive compositions. Such optional, i.e., non-essential constituents should be selected so to have little or no detrimental effect upon the desirable characteristics of the present invention, namely the blooming behavior, cleaning efficacy, hard surface cleaning activity, and low toxicity as provided by the inventive compositions. Generally the total weight of such further conventional additives may comprise up to 20% by weight of a concentrated composition formulation.

Further optional, but advantageously included constituents are one or more coloring agents which find use in modifying the appearance of the concentrate compositions and enhance their appearance from the perspective of a consumer or other end user. Known coloring agents, may be incorporated in the compositions in effective amount to improve or impart to concentrate compositions an appearance characteristic of a pine oil type concentrate composition, such as a color ranging from colorless to a deep amber, deep amber yellow or deep amber reddish color. Such a coloring agent or coloring agents may be added in any useful amount in a conventional fashion, i.e., admixing to a concentrate composition or blending with other constituents used to form a concentrate composition. However, other colors atypical of pine oil type cleaning concentrates may be used as well. Known art light stabilizer constituents useful in pine oil type compositions may also be added, particularly wherein coloring agents are used in a composition. As is known to the art, such light stabilizers act to retain the appearance characteristics of the concentrate compositions over longer intervals of time.

Exemplary useful buffers include the alkali metal phosphates, polyphosphates, pyrophosphates, triphosphates, tetraphosphates, silicates, metasilicates, polysilicates, carbonates, hydroxides, and mixtures of the same. Certain salts, such as the alkaline earth phosphates, carbonates, hydroxides, can also function as buffers. It may also be suitable to use buffers such materials as aluminosilicates (zeolites), borates, aluminates and certain organic materials such as gluconates, succinates, maleates, and their alkali metal salts. Such buffers keep the pH ranges of the compositions of the present invention within acceptable limits.

Exemplary useful pH adjusting agents include known materials which may be used to adjust the pH of the concentrate compositions to a desired range.

Useful optional detersive surfactants include anionic, nonionic, cationic and amphoteric surfactants which are found to not undesirably detract from the blooming characteristics of the present invention.

The useful optional nonionic surfactants, include known art nonionic surfactant compounds. Practically any hydrophobic compound having a carboxy, hydroxy, amido, or amino group with a free hydrogen attached to the nitrogen can be condensed with ethylene oxide or with the polyhydration product thereof, polyethylene glycol, to form a water soluble nonionic surfactant compound. Further, the length of the polyethylenoxy hydrophobic and hydrophilic elements may various. Exemplary nonionic compounds include the polyoxyethylene ethers of alkyl aromatic hydroxy compounds, e.g., alkylated polyoxyethylene phenols, polyoxyethylene ethers of long chain aliphatic alcohols, the polyoxyethylene ethers of hydrophobic propylene oxide polymers, and the higher alkyl amine oxides.

Exemplary useful nonionic surfactants in the compositions according to the present invention include commercially well known surfactant compositions.

Exemplary nonionic surfactants are certain ethoxylates presently commercially available under the trade name NEODOL (Shell Chemical Co., Houston, Tex. (USA)), which are ethoxylated higher aliphatic, primary alcohols. Such ethoxylates have an HLB (hydrophobic to lipophilic balance) value of about 8 to 15 and give good oil/water emulsification, whereas ethoxylates with HLB values below 8 contain less than 5 ethylene oxide groups and tend to be poor emulsifiers and poor detergents. Additional satisfactory nonionic surfactant compositions include the condensation products of a secondary aliphatic alcohols containing 8 to 18 carbon atoms in a straight or branched chain configuration condensed with 5 to 30 moles of ethylene oxide. Examples of commercially available nonionic detergents of the foregoing type are those presently commercially available under the trade name of TERGITOL (Union Carbide Co., Danbury, Conn. (USA)).

Other suitable nonionic surfactant compositions include the polyethylene oxide condensates of one mole of alkyl phenol containing from about 8 to 18 carbon atoms in a straight- or branched chain alkyl group with about 5 to 30 moles of ethylene oxide, including those which are presently commercially available under the trade name of IGEPAL (Rhône-Poulenc, Princeton N.J. (USA)). Further useful nonionic surfactants include the water-soluble condensation products of a $C_8$–$C_{20}$ alkanol with a mixture of ethylene oxide and propylene oxide wherein the weight ratio or ethylene oxide to propylene oxide is from 2.5:1 to 4:1, preferably 2.89:1 to 3.3:1, with the total of the ethylene oxide; and propylene oxide (including the terminal ethanol or proponol group) being from 60–85%, preferably 70 to 80%, by weight. Such include those commercially available under the trade name of PLURAFAC (BASF Corp., Hackettstown, N.J. (USA)). Still further useful water-soluble nonionic surfactants include condensation products of a $C_8$–$C_{20}$ alkanols with a mixture of ethylene oxide and/or propylene oxide. Such are commerically available under the tradename POLYTERGENT (Olin Chemical Co., Stamford Conn. (USA)).

Further suitable water-soluble nonionic surfactants which may also be used include those which are marketed under the trade name PLURONICS (BASF Corp., Hackettstown, N.J. (USA)). These are formed by condensing ethylene oxide with a hydrophobic base formed by the condensation of propylene oxide with propylene glycol. Further useful nonionic surfactants include Alkylmonoglyocosides and alkylpolyglycosides which are alkaline and electrolyte stable. Such are prepared generally by reacting a monosaccharide, or a compound hydrolyzable to a monosaccharide with an alcohol such as a fatty alcohol in an acid medium. Various glycoside and polyglycoside compounds including alkoxylated glycosides may be used. An exemplary useful polyglycoside is one according to the formula:

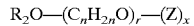

where Z is derived from glucose, R is a hydrophobic group selected from alkyl groups, alkylphenyl groups, hydroxyalkylphenyl groups as well as mixtures thereof, wherein the alkyl groups may be straight chained or branched, which contain from about 8 to about 18 carbon atoms, n is 2 or 3, r is an integer from 0 to 10, but is preferably 0, and x is a value from about 1 to 8, preferably from about 1.5 to 5. Preferably the alkylpolyglycosides are nonionic fatty alkylpolyglucosides which contain a straight chain or branched chain $C_8$–$C_{15}$ alkyl group, and have an average of from about 1 to about 5 glucose units per fatty alkylpolyglucoside molecule. More preferably, the nonionic fatty alkylpolyglucosides which contain straight chain or branched $C_8$–$C_{15}$ alkyl group, and have an average of from about 1 to about 2 glucose units per fatty alkylpolyglucoside molecule.

A further exemplary group of alkyl glycoside surfactants suitable for use in the practice of this invention may be represented by formula I below:

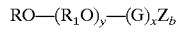

wherein: R is a monovalent organic radical containing from about 6 to about 30, preferably from about 8 to about 18 carbon atoms; $R_1$ is a divalent hydrocarbon radical containing from about 2 to about 4 carbon atoms; O is an oxygen atom; y is a number which has an average value from about 0 to about 1 and is preferably 0; G is a moiety derived from a reducing saccharide containing 5 or 6 carbon atoms; and x is a number having an average value from about 1 to 5 (preferably from 1.1 to 2); Z is $O_2M^1$,

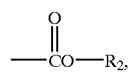

$O(CH_2)$, $CO_2M^1$, $OSO_3M^1$, or $O(CH_2)SO_3M^1$; $R_2$ is $(CH_2)$ $CO_2M^1$ or $CH=CHCO_2M^1$; (with the proviso that Z can be $O_2M^1$ only if Z is in place of a primary hydroxyl group in which the primary hydroxyl-bearing carbon atom, —$CH_2OH$, is oxidized to form a

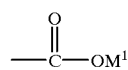

group); b is a number of from 0 to 3x+1 preferably an average of from 0.5 to 2 per glycosal group; p is 1 to 10, $M^1$ is $H^+$ or an organic or inorganic counterion, particularly cations such as, for example, an alkali metal cation, ammonium cation, monoethanolamine cation, or calcium cation.

As defined in Formula I above, R is generally the residue of a fatty alcohol having from about 8 to 30 and preferably 8 to 18 carbon atoms. Examples of such alkylglycosides as described above include, for example, APG™ 325 CS Glycoside® which is described as being a 50% $C_9$–$C_{11}$ alkyl polyglycoside, also commonly referred to as D-glucopyranoside, (commercially available from Henkel Corp, Ambler Pa.) and Glucopon™ 625 CS which is described as being a 50% $C_{10}$–$C_{16}$ alkyl polyglycoside, also commonly referred to as a D-glucopyranoside, (available from Henkel Corp., Ambler Pa.).

Further exemplary useful nonionic surfactants which may be used include certain alkanolamides including monoethanolamides and diethanolamides, particularly fatty monoalkanolamides and fatty dialkanolamides. Commercially available monoethanol amides and diethanol amides include those marketed under the trade names Alakamide® and Cyclomide® by Rhône-Poulenc Co., (Cranbury, N.J.).

The nonionic surfactants, when present, can be present either singly, or as a mixture of two or more nonionic surfactant compounds as defined above.

Exemplary anionic surfactants include compounds known to the art as useful as anionic surfactants. These include but are not limited to: alkali metal salts, ammonium salts, amine salts, aminoalcohol salts or the magnesium salts of one or more of the following compounds: alkyl sulfates, alkyl ether sulfates, alkylamidoether sulfates, alkylaryl polyether sulfates, monoglyceride sulfates, alkylsulfonates, alkylamide sulfonates, alkylarylsulfonates, olefinsulfonates, paraffin sulfonates, alkyl sulfosuccinates, alkyl ether sulfosuccinates, alkylamide sulfosuccinates, alkyl sulfosuccinamate, alkyl sulfoacetates, alkyl phosphates, alkyl ether phosphates, acyl sarconsinates, acyl isethionates, and N-acyl taurates. Generally, the alkyl or acyl radical in these various compounds comprise a carbon chain containing 12 to 20 carbon atoms.

Further exemplary anionic surface active agents which may be used include fatty acid salts, including salts of oleic, ricinoleic, palmitic, and stearic acids; copra oils or hydrogenated copra oil acid, and acyl lactylates whose acyl radical contains 8 to 20 carbon atoms.

More specific examples of suitable alkyl aromatic sulfonate detergents include the straight chain linear alkyl benzene sulfonates wherein the alkyl group contains 10 to 18 carbon atoms, e.g., averaging about 10 to 15, specific examples of which are sodium dodecyl benzene sulfonate, sodium tridecyl benzene sulfonate and sodium higher alkyl benzene sulfonate wherein the alkyl is of 10 to 15 carbon atoms, averaging about 12.5 carbon atoms per molecular proportion.

Other suitable agents are the surface-active sulfated or sulfonated aliphatic compounds, preferably of 12 to 22 carbon atoms. Within the scope of such definition are the sulfuric acid esters of polyhydric alcohols incompletely esterified with higher fatty acids, e.g., coconut oil monoglyceride monosulfate, tallow diglyceride monosulfate; the long chain pure or mixed alkyl sulfates, e.g., lauryl sulfate, cetyl sulfate; the hydroxysulfonated higher fatty acid esters, such as the higher fatty acid esters of low molecular weight alkyl sulfonic acids, e.g., fatty acid esters of isethionic acid; the fatty acid ethanolamide sulfates; the fatty acid amides of aminoalkyl sulfonic acids, e.g., the lauric acid amide of taurine; olefin and paraffin sulfonates; and the like. More particularly, it is preferred to use the sulfated aliphatic compounds containing at least about 8 carbon atoms, especially those having about 12 to about 18 or 22 carbon atoms in the molecule.

Preferred to use the aliphatic sulfates and sulfonates of about 8 to 22 carbon atoms and the alkyl aromatic sulfonates containing about 8 to about 22 carbon atoms in the alkyl group, preferably of 12 to 18 carbon atoms.

For the synthetic anionic compounds, the alkali metal (e.g., sodium, potassium) salts are preferred, although other salts such as ammonium, lower alkyl amine, i.e., straight or branched chain mono-, di and trialkylamines of 1 to 4 carbons in the alkyl group e.g., methyl amine diisopropyl amine and tributyl amine; lower alkanolamine, e.g., ethanolamine, diethanolamine, triethanolamine and isopropanolamine; and alkaline earth and similar metal, e.g., calcium and magnesium salts; may be used, if desired.

Other anionic surface active agents not particularly enumerated here may also find use in conjunction with the compounds of the present invention.

Exemplary cationic surface active agents include, by way of non-limiting example, include those which include charged nitrogen containing compounds such as quaternary ammonium compounds, as well as others known to the art. An exemplary and preferred cationic compound quaternary ammonium compounds and salts thereof, which may be characterized by the general structural formula:

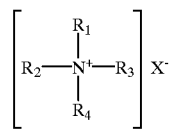

where at least one of $R_1$, $R_2$, $R_3$ and $R_4$ is a alkyl, aryl or alkylaryl substituent of from 6 to 26 carbon atoms, and the entire cation portion of the molecule has a molecular weight of at least 165. The alkyl substituents may be long-chain alkyl, long-chain alkoxyaryl, long-chain alkylaryl, halogen-substituted long-chain alkylaryl, long-chain alkylphenoxyalkyl, arylalkyl, etc. The remaining substituents on the nitrogen atoms other than the abovementioned alkyl substituents are hydrocarbons usually containing no more than 12 carbon atoms. The substituents $R_1$, $R_2$, $R_3$ and $R_4$ may be straight-chained or may be branched, but are preferably straight-chained, and may include one or more amide, ether or ester linkages. The counterion X may be any salt-forming anion which permits water solubility of the quaternary ammonium complex. Certain of these quaternary ammonium compounds may exhibit a germicidal effect, but this is not essential to the present invention.

Exemplary amphoteric surface active agents include, by way of non-limiting example, As further useful optional constituent, the inventive compositions may also include one or more further known art surfactant compositions, including betaines, ethylene oxide condensates, and fatty acid amides.

Exemplary useful betaine surfactants include those according to the general formula:

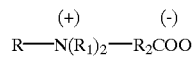

wherein R is a hydrophobic group selected from the group consisting of alkyl groups containing from about 10 to about 22 carbon atoms, preferably from about 12 to about 18 carbon atoms, alkyl aryl and aryl alkyl groups containing a similar number of carbon atoms with a benzene ring being treated as equivalent to about 2 carbon atoms, and similar structures interrupted by amido or ether linkages; each $R_1$ is an alkyl group containing from 1 to about 3 carbon atoms; and $R_2$ is an alkylene group containing from 1 to about 6 carbon atoms.

Examples of preferred betaines are dodecyl dimethyl betaine, cetyl dimethyl betaine, dodecyl amidopropyldimethyl betaine, tetradecyldimethyl betaine, tetradecylamidopropyldimethyl betaine, and dodecyldimethylammonium hexanoate.

Useful fatty acid amides include those which are known to the art. Particular exemplary fatty acid amide surfactants include ammonia, monoethanol, and diethanol amides of fatty acids having an acyl moiety which contains from about 8 to about 18 carbon atoms, and which may be represented in accordance with the formula:

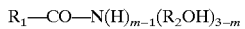

where $R_1$ represents a saturated or unsaturated aliphatic hydrocarbon radical of from about 7 to 21 carbon atoms, but preferably from about 11 to 17 carbon atoms; $R_2$ represents a —CH$_2$— or —CH$_2$CH$_2$—, and m is an integer from 1 to 3, but is preferably 1. Preferably, R$_1$ is a saturated or unsaturated aliphatic hydrocarbon radical comprising from about 11 to 17 carbon atoms, and m is 1.

Further examples of such compounds include monoethanol amine coconut fatty acid amide and diethanol amine dodecyl fatty acid amide. An exemplary useful fatty acid amide includes cocomonoethanol amide or cocodiethanolamide, which are presently commercially available as MONAMID CMA (Mona Industries, Paterson N.J. (USA)).

What is to be understood by the term "concentrate" and "concentrate composition" in this specification and claims is the pre-consumer dilution and composition of the cleaning composition which is the essentially the form of the product prepared for sale to the consumer or other end user. Such a consumer or other end user would then normally be expected to dilute the same with water to form a cleaning composition. It is to be understood however that nothing in this invention would bar its use as cleaning composition without any further dilution and it may be used in the concentrations in which it was prepared for sale. Similarly, what is to be understood by the term "cleaning compositions" are the water diluted compositions which are expected to be prepared by the consumer or other end user by mixing a measured amount of the "concentrate" with water in order to form an appropriately diluted cleaning composition which is suitable for use in cleaning applications, especially in the cleaning of hard surfaces.

It is also to be understood, that proportions of one or more constituents have been and generally are referred to as percent by weight or as parts by weight based on a measure of 100% by weight, unless otherwise indicated.

According to certain particularly preferred embodiments of the invention there are provided aqueous concentrated liquid hard surface cleaning composition which comprise the following constituents:

1–10% wt. of pine oil constituent;
0.1–35% wt. of an organic solvent constituent;
0.1–12% wt. of a binary co-solvent system comprising alkyl biphenyl solvent and a co-solvent;
1–20% wt. of an amine oxide surfactant constituent;
to 100% wt. of water, and;
optionally but desirably up to 20% wt. of at least one optional constituent selected from: chelating agents, coloring agent, light stabilizers, fragrances, thickening agents, hydrotropes, pH adjusting agents, pH buffers one or more detersive surfactant constituents.

As generally denoted above, the formulations according to the invention include both cleaning compositions and concentrates as outlined above which differ only in the relative proportion of water to that of the other constituents forming such formulations. While the concentrated form of the cleaning compositions find use in their original form, they are more frequently used in the formation of a cleaning composition therefrom. Such may be easily prepared by diluting measured amounts of the concentrate compositions in water by the consumer or other end user in certain weight ratios of concentrate:water, and optionally, agitating the same to ensure even distribution of the concentrate in the water. As noted, the concentrate may be used without dilution, i.e., in concentrate:water concentrations of 1:0, to extremely dilute dilutions such as 1:10,000. Desirably, the concentrate is diluted in the range of 1:0.1–1:1000, preferably in the range of 1:1–1:500 but most preferably in the range of 1:10–1:100. The actual dilution selected is in part determinable by the degree and amount of dirt and grime to be removed from a surface(s), the amount of mechanical force imparted to remove the same, as well as the observed efficacy of a particular dilution. Generally better results and faster removal is to be expected at lower relative dilutions of the concentrate in water.

In accordance with preferred embodiments of the invention, when a quantity of the concentrate compositions taught herein are added to a larger volume of water, a blooming characteristic is manifested. Such "blooming" may be broadly characterized as the formation of milky, creamy or cloudy appearance which is manifested when a dilutable composition is added to a larger volume or quantity of water. Such "blooming" may be alternately characterized as the reduction of transmitted light through an amount of water by at least 30%, desirably by at least 40%, yet more desirably by at least about 50%, and yet most desirably by at least 60% or more when a dilution of the concentrate composition:water with the weight or volume ratio range of from 1:64–102 is formed. That such blooming may be attained without the use of pine oil fractions as is common in certain commercially available pine oil containing preparations is surprising.

As has been noted, concentrate compositions according to preferred embodiments of the invention exhibit a long lasting blooming effect when they are diluted into a larger volume of water, especially when used to form (weight ratio) dilutions with water of concentrate:water of 1:64 at room temperature. Desirably, such dilutions do not exhibit an increase in light transmittance in accordance with the measurement methods discussed in the Examples below, of more than 50% (based on the initial 'as mixed' value) during its initial three-day interval.

The concentrate compositions according to the invention, and aqueous dilutions formed therefrom, are particularly useful in the cleaning of hard surfaces. By way of non-limiting example, hard surfaces include surfaces composed of refractory materials such as: glazed and unglazed tile, brick, porcelain, ceramics as well as stone including marble, granite, and other stones surfaces; glass; metals; plastics e.g. polyester, vinyl; fiberglass, Formica®, Corian® and other hard surfaces known to the art. Hard surfaces which are to be particularly denoted include those associated with kitchen environments, lavatory environments, especially flooring surfaces and the surfaces of fixtures (doors, cabinets, shelving, and the like) in such environments.

Such dilution ratios of concentrate:water as described above may be volume/volume basis, or a weight/weight basis.

The following examples below illustrate exemplary and among them preferred formulations of the composition according to the instant invention. It is to be understood that these examples are presented by means of illustration only and that further useful formulations fall within the scope of this invention and the claims may be readily produced by one skilled in the art and not deviate from the scope and spirit of the invention.

EXAMPLES

A number of formulations were produced by mixing the constituents outlined in Table 1 by adding the individual constituents into a beaker of deionized water at room temperature which was stirred with a conventional magnetic stirring rod. The order of addition is not critical, but good results are obtained where the surfactants are added to the water prior to Stirring continued until the formulation was homogenous in appearance. It is to be noted that the constituents might be added in any order, but it is preferred that water be the initial constituent provided to a mixing vessel or apparatus as it is the major constituent and addition of the further constituents thereto is convenient. The exact compositions of the example formulations are listed on Table 1, below. Attention is directed to the fact that the formulations in Table 1 were substantially the same, except for the types and amounts of acids which were included in the formulations.

TABLE 1

| Notebook Ref: | Ex. 1 | Ex. 2 | Ex. 3 | Ex. 4 | Ex. 5 | Ex. 6 | Ex. 7 |
|---|---|---|---|---|---|---|---|
| Pine Oil 80 | 8.30 | 8.30 | 4.00 | 4.00 | 4.00 | 4.00 | 4.00 |
| Isopropyl alcohol | 12.00 | 12.00 | 12.00 | 12.00 | 12.00 | 12.00 | 12.00 |
| Na2EDTA | 0.50 | 0.50 | 0.50 | — | 0.50 | 0.50 | 0.50 |
| propylene glycol | 20.00 | 20.00 | 20.00 | 20.00 | 20.00 | 20.00 | 20.00 |
| lauryl alcohol | 1.00 | 1.00 | 1.00 | 1.00 | 1.00 | 1.00 | 1.00 |
| Tomah AO-728 special (50%) | 14.00 | — | 14.00 | 14.00 | 14.00 | 14.00 | 14.00 |
| Ammonyx CDO (30%) | — | 15.00 | — | — | — | — | — |
| biphenyl solvent A | 1.00 | 1.00 | 4.00 | 4.00 | 4.00 | — | — |
| biphenyl solvent B | — | — | — | — | — | 4.00 | — |
| biphenyl solvent C | — | — | — | — | — | — | 4.00 |
| alkylpolyoxycarboxylate | — | — | — | 0.50 | — | — | — |
| Colorant | 0.03 | 0.03 | 0.03 | 0.03 | 0.03 | 0.03 | 0.03 |
| di water | q.s. | q.s. | q.s. | q.s. | q.s. | q.s. | q.s. |

TomahAO-728 (50%) was bis(2-hydroxyethyl $C_{12}$–$C_{15}$ alkyloxypropyl) amine oxide (50% wt. actives)
Ammonyx CDO (30%) was cocoamidopropyl dimethylamine oxide (30% wt. actives)
biphenyl solvent A was NUSOLV ABP-103 (Arristec, Inc.) is a mixture of alkyl biphenyls
biphenyl solvent B was SURE SOL 300 (Koch Chemical Co.) is a mixture of alkyl biphenyls, specifically diisopropyl biphenyls (65%), triisopropyl biphenyls (30%) and other alkyl biphenyls (5%)
biphenyl solvent C was SURE SOL 330 (Koch Chemical Co.) is a mixture of alkyl biphenyls
alkylpolyoxycarboxlate was Emcol CNP 110 (Witco Chem. Co.) which aids in solublizing the alkyl biphenyls in water
Na2EDTA was the disodium salt of ethylenediaminetetraacetic acid
di water was deionized water All of the formulations on Table 1 indicated in weight percent, and the percent actives of individual constituents are 100% unless otherwise indicated.

The blooming characteristics of these formulations was characterized by using the Brinkman Sybron PC 801 calorimeter. Each tested formulation were diluted with deionised water in a weight ratio of 1:64, and the test was carried out with each of the formulations and water at room temperature (68° F., 20° C.). The resulting determined values, reported as "blooming" in the following table provide an empirical evaluation in percent transmittance (%) of the degree of transparency of a diluted example formulation wherein 0% indicates complete opacity and 100% the transparency of a deionised water sample. The result was tabulated as follows:

TABLE 2

| | % Transmittance |
|---|---|
| Comp. 1 | 0.5 |
| Ex. 1 | 2.4 |
| Ex. 2 | 3.1 |
| Ex. 3 | 0.7 |
| Ex. 4 | 0.9 |
| Ex. 5 | 0.5 |
| Ex. 6 | 0.7 |
| Ex. 7 | 0.9 |

Comparative 1 (Comp. 1) was DETTOL (Reckitt & Colman PLC, Hull, UK), a soap based, blooming type disinfecting concentrate composition which does not include biphenyl solvents. DETTOL has a particularly substantive bloom and is used as a 'benchmark' for other formulations.

As may be seen from the results indicated on Table 2, the formulations according to the invention (Ex.1, Ex.2, Ex.3) which included the biphenyl solvent indicated blooming which was very similar to Comparative Example 1 (Comp.1), which is a control formulation. Importantly, not only was the intensity of the bloom of each of the formulations according to the invention excellent, but the degree of light transmittance did not decrease over a 1 week, an important indicator of the superior duration and stability of the inventive blooming type compositions.

The formulation of Ex.3, 4 and 5 were diluted with deionised water in a weight ratio of 1:64, at room temperature (68° F., 20° C.), and the degree of transparency was determined using the apparatus and method described above. For comparative purposes, a formulation ("Comp.2") from the prior art, namely Ex. 3 from Table 1 of U.S. Pat. No. 5,629,280 was prepared in accordance with the teaching in that patent, and similarly diluted and tested as the formulation according to Ex. 3, 4 and 5. Each of the diluted formulations were evaluated over an eight day period at intervals so to determine the long term blooming behavior of the respective compositions. All of the formulations and compositions were maintained at room temperature (68° F., 20° C.) throughout the duration of the test. The results are indicated on Table 3.

TABLE 3

| | % Light Transmittance | | | |
|---|---|---|---|---|
| Day: | Ex. 3 | Ex. 4 | Ex. 5 | Comp. 2 |
| Initial (as mixed) | 0.3 | 3.0 | 0.3 | 5.9 |
| Day 1 | 0.3 | 3.7 | 0.4 | 24.1 |
| Day 2 | — | — | — | 29.6 |
| Day 3 | — | — | — | 49.9 |
| Day 4 | 0.6 | 1.6 | 0.5 | — |
| Day 5 | 0.5 | 1.5 | 0.7 | — |
| Day 6 | 0.3 | 1.4 | 0.5 | 76.1 |
| Day 7 | 0.4 | 1.3 | 0.5 | — |
| Day 8 | — | — | — | 86.5 |

Comparative 2 (Comp. 2) was Ex. 3 from Table 1 of US 5629280 "—" indicates not tested, as it was visually observed that no discernible change had occurred since the previous test As the results of Table 3 indicate, the compositions according to the present invention provided superior results, both with respect to initial blooming property in the "as mixed" dilutions, and significantly, also maintained excellent blooming characteristics over a longer duration.

Cleaning Test

Cleaning efficacy was measured for weight ratios of 1:64 (concentrate composition:water) aqeuous dilutions of formulations according to Ex.1, 2 and 3 and as a control, the formulation according to Comp.2 described above. The test was carried out using the ASTM D4488-89, Annex A2 method—greasy soil on painted masonite wallboard test, using a Gardner Washability Apparatus.

Latex painted masonite wallboard is soiled with a mixture of melted, oily soils containing a small amount of carbon black and allowed to set overnight. A first aqueous dilution is applied to a sponge that scrubs half the soiled substrate in a straight-line using the Gardner Washability Apparatus. Afterwards, the second aqueous dilution is applied to a further sponge that scrubs the other half of the soiled substrate in a similar manner.

In determining the cleaning efficiency, reflectance values were determined using a Gardner Lab Scan Reflectometer for each of the following: a clean unsoiled panel, a soiled panel, and a soiled panel following Gardner Washability Apparatus scrubbing. Such reflectance values were then employed to calculate % cleaning efficiency according to the following formula:

$$\% \text{ Cleaning Efficiency} = \frac{Lt - Ls}{Lo - Ls} \times 100\%$$

wherein,
Lt=% reflectance average after scrubbing solid tile
Ls=% reflectance average before cleaning soiled tile
Lo=% reflectance average original tile before soiling
Cleaning efficiency results for Formulation 1 are shown in TABLE 4, hereinafter.

TABLE 4

| Test # | Formulation: water (1:64) w/w dilution | unsoiled reflectance (Lo) | soiled reflectance (Ls) | After scrubbing reflectance (Lt) | % Cleaning Efficiency |
|---|---|---|---|---|---|
| Comp. 1 | 1:64 | 94.09 | 24.89 | 65.26 | 58.34 |
| Ex. 1 | 1:64 | 94.09 | 24.89 | 66.41 | 60.00 |
| Ex. 2 | 1:64 | 94.09 | 24.89 | 60.49 | 51.45 |
| Ex. 3 | 1:64 | 94.09 | 24.89 | 63.06 | 55.16 |

Comparative 1 (Comp. 1) was DETTOL (Reckitt & Colman PLC, Hull, UK)

As shown, the measurement of the cleaning effectiveness of the test samples involved the ability of the cleaning composition to remove the test soil from the test substrate. This was expressed by % Cleaning Efficiency. As numerical values for a % Cleaning Efficiency increase, higher cleaning effectiveness is achieved for the cleaning composition tested. As the results show, the inventive composition showed an excellent cleaning property.

What is claimed is:

1. An aqueous concentrated liquid hard surface cleaning composition which blooms when added to a larger volume of water which comprises:
   pine oil constituent;
   organic solvent constituent;
   binary co-solvent system comprising an alkyl biphenyl solvent and a co-solvent;
   an amine oxide surfactant constituent;
   optionally at least one optional constituent selected from: chelating agents, coloring agents, light stabilizers, fragrances, thickening agents, hydrotropes, pH adjusting agents, pH buffers one or more detersive surfactant constituents including non-ionic and amphoteric surfactants and the balance, water.

2. The aqueous concentrated composition according to claim 1 wherein the pine oil constituent comprises at least 60% terpene alcohols.

3. The aqueous concentrated composition according to claim 1 wherein the amine oxide constituent is represented by the formula:

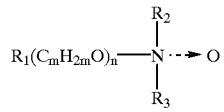

wherein $R_1$ is hydrogen or is an alkyl, 2-hydroxyalkyl, 3-hydroxyalkyl, or 3-alkoxy-2-hydroxypropyl radical where the alkyl and alkoxy parts contain from about 8 to about 18 carbon atoms, $R_2$ and $R_3$ are independently selected from methyl, ethyl, propyl, isopropyl, 2-hydroxyethyl, 2-hydroxypropyl, or 3-hydroxypropyl, m is an integer from 2 to 4, and n is an integer from 0 to 10.

4. The aqueous concentrated composition according to claim 1 wherein the amine oxide constituent is represented by the formula:

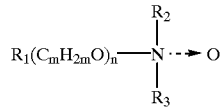

wherein, $R_1$ is an alkyl radical of from 12 to 16 carbon atoms, $R_2$ and $R_3$ are independently selected from methyl or ethyl, m is 2, and n is 0.

5. The aqueous concentrated composition according to claim 1 wherein the alklyl biphenyl solvent is represented according to the structure:

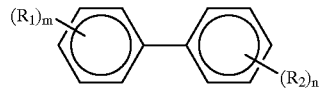

wherein:

$R_1$ is a lower alkyl radical, $R_2$ is a lower alkyl radical, m is an integer from 0–3 inclusive; and, n is an integer from 1–3 inclusive.

6. The aqueous concentrated composition according to claim 5 wherein:

$R_1$ is hydrogen, m is 1, n is an integer from 1–3 inclusive, and, $R_2$ is a $C_1$–$C_6$ straight chained or branched alkyl radical.

7. An aqueous concentrated composition which blooms when added to a larger volume of water which comprises:

1–10% wt. of pine oil constituent;

0.1–35% wt. of an organic solvent constituent;

0.1–12% wt. of a binary co-solvent system comprising alkyl biphenyl solvent and a co-solvent;

1–20% wt. of an amine oxide surfactant constituent;

to 100% wt. of water, and;

optioxally up to 20% wt. of at least one optional constituent selected from: chelating agents, coloring agents, light stabilizers, fragrances, thickening agents, hydrotropes, pH adjusting agents, pH buffers one or more detersive surfactant constituents including non-ionic and amphoteric surfactants, as well as others known the art.

8. An aqueous concentrated composition according to claim 1 characterized in that when the said concentrated composition is diluted with water at a weight ratios of concentrate:water of 1:64 at room temperature, the resultant composition exhibits a reduction in light transmittance of at least 50%.

9. The aqueous concentrated composition according to claim 5 wherein:

$R_1$ is a $C_1$–$C_{10}$ alkyl radical.

10. The aqueous concentrated composition according to claim 9 wherein:

$R_1$ is a $C_1$–$C_6$, straight chained or branched alkyl radical.

11. The aqueous concentrated composition according to claim 5 wherein:

$R_2$ is a $C_1$–$C_{10}$ alkyl radical.

12. The aqueous concentrated composition according to claim 11 wherein:

$R_2$ is a $C_1$–$C_6$ straight chained or branched alkyl radical.

* * * * *